United States Patent
Xiang et al.

(10) Patent No.: US 10,580,515 B2
(45) Date of Patent: Mar. 3, 2020

(54) SYSTEMS AND METHODS FOR GENERATING BIOMARKER SIGNATURES

(71) Applicant: Philip Morris Products S.A., Neuchatel (CH)

(72) Inventors: Yang Xiang, Neuchatel (CH); Julia Hoeng, Corcelles (CH)

(73) Assignee: Philip Morris Products S.A. (CH)

( * ) Notice: Subject to any disclaimer, the term of this patent is extended or adjusted under 35 U.S.C. 154(b) by 844 days.

(21) Appl. No.: 14/409,675

(22) PCT Filed: Jun. 21, 2013

(86) PCT No.: PCT/EP2013/062984
§ 371 (c)(1),
(2) Date: Dec. 19, 2014

(87) PCT Pub. No.: WO2013/190086
PCT Pub. Date: Dec. 27, 2013

(65) Prior Publication Data
US 2015/0193577 A1 Jul. 9, 2015

Related U.S. Application Data (60) Provisional application No. 61/662,658, filed on Jun. 21, 2012.

(51) Int. Cl.
*G01N 33/48* (2006.01)
*G01N 33/50* (2006.01)
(Continued)

(52) U.S. Cl.
CPC ............ *G16B 25/00* (2019.02); *G16B 35/00* (2019.02); *G16B 40/00* (2019.02); *G16C 20/60* (2019.02)

(58) Field of Classification Search
None
See application file for complete search history.

(56) References Cited

U.S. PATENT DOCUMENTS 7,370,021 B2 5/2008 Reeve et al.
2003/0195706 A1* 10/2003 Korenberg .............. G06F 19/20
702/19

(Continued)

FOREIGN PATENT DOCUMENTS

JP 2005-325771 A 11/2005
JP 2006-323830 A 11/2006

OTHER PUBLICATIONS

Singh et al. Gene expression correlates of clinical prostate cancer behavior. Cancer Cell, vol. 1, pp. 203-209. (Year: 2002).*

(Continued)

*Primary Examiner* — Russell S Negin
(74) *Attorney, Agent, or Firm* — Sterne, Kessler, Goldstein & Fox P.L.L.C.

(57) ABSTRACT

The systems and methods described herein include a technique for generating both reproducible and interpretable gene signatures. The technique involves resampling a data set and choosing genes having a high frequency of emergence. In particular, the systems and methods described herein include repeated sampling of data sets, ranking genes based on frequency of occurrence in gene signatures generated through the repeated sampling process, and iteratively selecting the best gene signature.

14 Claims, 6 Drawing Sheets

(51) Int. Cl.
*G16B 25/00* (2019.01)
*G16B 35/00* (2019.01)
*G16B 40/00* (2019.01)
*G16C 20/60* (2019.01)

(56) References Cited

U.S. PATENT DOCUMENTS

2003/0207278 A1* 11/2003 Khan .................. G06F 19/20
 435/6.14
2004/0076984 A1 4/2004 Eils
2008/0031816 A1 2/2008 Keller

OTHER PUBLICATIONS

"The Fuzzy Gene Filter: An Adaptive Fuzzy Inference System for Expression Array Feature Selection", Trends in Applied Intelligent systems, Springer Berlin Heidelbert, Jun. 1, 2010, pp. 62-71.
"Assessing stability of gene selection in microarray data analysis", Xing, Qiu, et al., BMC Bioinformatics, Biomed Central, London, GB, vol. 7, No. 1, Feb. 1, 2006.
"Recognition and Classification of Histones Using Support Vector Machine", Bhasin, Manoj et al., Journal of Computational Biology, vol. 13, No. 1., Jan. 1, 2006.
"Wikipedia: Cross-validation (statistics)", Anonymous, May 12, 2012, retrieved from the Internet: URL:http://en.wikipedia.org/w/index.php?title=Special:Book&bookcmd=download&collection_id=60a967523a4eb919&writer=rl&return_to=Cross-validation(statistics) (retrieved on Oct. 15, 2013).
"Gene selection for sample classification based on gene expression data: Study of sensitivity to choice of parameters of the GA/KNN method", Li, L., et al., Bioinformatics, Oxford University Press, Surrey, GB, vol. 17, No. 12, Dec. 1, 2001, pp. 1131-1142.
"Application of the GA/KNN method to SELDI proteomics data", Li, L., et al., Bioinformatics, vol. 20, No. 10, Jul. 1, 2004, pp. 1638-1640.
"Feature Selection and Molecular classification of Cancer Using Genetic Programming", Yu, Jianjun et al., Neoplasia, vol. 9, No. 4, Apr. 1, 2007, pp. 292-303.
International Search Report and Written Opinion dated Nov. 13, 2013 in International Application No. PCT/EP2013/062984.
International Preliminary Report on Patentability directed to related International Patent Application No. PCT/EP2013/062984, dated Dec. 23, 2014; 10 pages.
English-language abstract of Japanese Patent Application Publication No. 2005-325771 A, published Nov. 24, 2005; 1 page.
English-language abstract of Japanese Patent Application Publication No. 2006-323830 A, published Aug. 12, 2004; 1 page.

* cited by examiner

SYSTEMS AND METHODS FOR GENERATING BIOMARKER SIGNATURES

CROSS REFERENCE TO RELATED APPLICATIONS

This application is a U.S. Nationalization of PCT Application No. PCT/EP2013/062984 filed Jun. 21, 2013, which claims the benefit of U.S. Provisional Application No. 61/662,658, filed Jun. 21, 2012, the entireties of which are incorporated herein by reference.

BACKGROUND

In the biomedical field it is important to identify substances that are indicative of a specific biological state, namely biomarkers. As new technologies of genomics and proteomics emerge, biomarkers are becoming more and more important in biological discovery, drug development and health care. Biomarkers are not only useful for diagnosis and prognosis of many diseases, but also for understanding the basis for development of therapeutics. Successful and effective identification of biomarkers can accelerate the new drug development process. With the combination of therapeutics with diagnostics and prognosis, biomarker identification will also enhance the quality of current medical treatments, thus play an important role in the use of pharmacogenetics, pharmacogenomics and pharmacoproteomics.

Genomic and proteomic analysis, including high throughput screening, supplies a wealth of information regarding the numbers and forms of proteins expressed in a cell and provides the potential to identify for each cell, a profile of expressed proteins characteristic of a particular cell state. In certain cases, this cell state may be characteristic of an abnormal physiological response associated with a disease. Consequently, identifying and comparing a cell state from a patient with a disease to that of a corresponding cell from a normal patient can provide opportunities to diagnose and treat diseases.

These high throughput screening techniques provide large data sets of gene expression information. Researchers have attempted to develop methods for organizing these data sets into patterns that are reproducibly diagnostic for diverse populations of individuals. One approach has been to pool data from multiple sources to form a combined data set and then to divide the data set into a discovery/training set and a test/validation set. However, both transcription profiling data and protein expression profiling data are often characterized by a large number of variables relative to the available number of samples.

Observed differences between expression profiles of specimens from groups of patients or controls are typically overshadowed by several factors, including biological variability or unknown sub-phenotypes within the disease or control populations, site-specific biases due to difference in study protocols, specimens handling, biases due to differences in instrument conditions (e.g., chip batches, etc.), and variations due to measurement error.

Several computer-based methods have been developed to find a set of features (markers) that best explain the difference between the disease and control samples. Some early methods included statistical tests such as LIMMA, the FDA approved mammaprint technique for identifying biomarkers relating to breast cancer, logistical regression techniques and machine learning methods such as support vector machines (SVM). Generally, from a machine learning perspective, the selection of biomarkers is typically a feature selection problem for a classification task. However, these early solutions faced several disadvantages. The signatures generated by these techniques were not reproducible because the inclusion and exclusion of subjects can lead to different signatures. These early solutions were also not robust because they operated on datasets having small sample sizes and high dimensions. Additionally, the signatures generated by these techniques included many false positives and were difficult to interpret in a biological way because neither the technique nor the gene signatures themselves shed any light on the underlying biological mechanisms. Consequently, because they are not reproducible and are difficult to interpret, they may not be especially useful for clinical diagnosis.

More recent techniques involve the integration of knowledge about canonical pathways and protein-protein interactions into gene selection algorithms. Also, several feature selection techniques have been developed, and these include filter methods, wrapper methods and embedded methods. Filter methods work independently of classifier design and perform feature selection by looking at the intrinsic properties of the data. Wrapper and embedded methods perform feature selection by making use of a specific classification model. The Wrapper method uses a search strategy in the space of possible feature subsets, guided by predictive performance of a classification model. Embedded methods make use of the classification model internal parameters to perform feature selection. However, these techniques also face several disadvantages.

Accordingly there is a need for an improved technique for identifying biomarkers for clinical diagnosis, prognosis or both.

SUMMARY

As noted above, early solutions as well as newer embedded and wrapper methods face several disadvantages. In particular, Applicants have recognized that these methods depend on the specific type of classification method used. In other words, if the classification method is not fit for the type of user data, these methods generally tend to fail or perform poorly. Applicants have further recognized that an ensemble of methods tends to outperform an individual method. The computer systems and computer program products described herein implement methods that include one or more such ensemble techniques and including techniques for generating both reproducible and interpretable gene signatures. The technique involves resampling a data set and choosing genes having a high frequency of emergence. In particular, the computer-implemented methods described herein include repeated sampling of data sets, ranking genes based on frequency of occurrence in gene signatures generated through the repeated sampling process, and iteratively selecting the best gene signature.

In certain aspects, the systems and methods described herein include means and methods for identifying a biological signature or a set of biomarkers, for a disease condition. The methods may comprise receiving a plurality of data sets, each data set comprising activity or expression level data for each of a plurality of biological entities in a biological system. The biological system can be in one of several states. For example, the biological system may be in a perturbed state caused by an exposure to a substance. In another example, the biological system may be in a state of a disease condition, or in a state that is of a control or normal condition. The methods may further comprise a plurality of iterations, for each iteration, splitting the plurality of data sets into a training portion and a test portion. The training portion of the plurality of data sets may be used to determine a differential expression for each biological entity by comparing the expression levels corresponding to two different states of the biological system (e.g., disease state and normal state). Furthermore, the training portion may be used to store, as a sub-candidate signature, a predetermined number of biological entities in the training portion with differential expressions above a threshold. The training portion may also be used to generate a classification rule that assigns each of the data sets to one of a disease class and a normal or control class based on the expression levels of the identified biological entities within the data set.

For each of the plurality of iterations, the methods may also comprise using the test portion of the plurality of data sets for applying the classification rule to assign each data set to one of the disease class and the normal/control class, and generating a performance sub-measure for the subcandidate signature by comparing the assignment for each data set against the state of the biological system associated with the data set. In certain embodiments, the methods include generating a candidate signature with the predetermined number of biological entities by selecting biological entities that rank high frequently from an aggregation of the sub-candidate signatures, and generating a performance measure associated with the candidate signature based on the performance sub-measures. In certain embodiments, the methods include repeating one or more of the above steps for a plurality of different values of the predetermined number to generate a plurality of candidate signatures and a plurality of associated performance measures. Then, the candidate signature associated with a highest performance measure or a performance measure that exceeds some threshold is stored as the biological signature.

In certain embodiments of the methods described above, the plurality of biological entities comprises one or more of genes and miRNA. The expression level may comprise one or more of methylation data, gene expression data, miRNA expression data and protein expression data. In certain embodiments of the methods described above, the step of determining a differential expression comprises at least one of a Significance Analysis of Microarrays (SAM) analysis and a Limma analysis. Limma may be preferred over SAM because Limma is associated with greater efficiency and lower demand on computing power. In certain embodiments of the methods, the step of generating a classification rule may comprise a support vector machine method. In general, the classifier may include network-based support vector machines, neural network-based classifiers, logistic regression classifiers, decision tree-based classifiers, classifeirs employing a linear discriminant analysis technique, a random-forest analysis technique, or a combination of the foregoing.

In certain embodiments of the methods, the step of generating the performance sub-measure may comprise calculating the percentage of data sets correctly assigned. In certain embodiments of the methods, the step of generating the performance sub-measure comprises calculating a Matthews correlation coefficient of the assigned data sets. In certain embodiments of the methods, the aggregation of the sub-candidate signatures may comprise a set union of all of the biological entities included in the sub-candidate signatures. In certain embodiments of the methods, the step of generating the performance measure may also comprise averaging all of the performance sub-measures for the subcandidate signatures associated with the predetermined number. In certain embodiments of the methods, the method further comprises displaying a graph of the plurality of performance measures against the plurality of different values of the predetermined number, and optionally a list of the biological entities included in the candidate signature. In certain embodiments, the methods include displaying, on a display device, a graph of the plurality of performance measures against the plurality of different values of the predetermined number. The methods may also include displaying, on a display device, a list of the biological entities included in the candidate signature.

The computer systems of the present invention comprise means for implementing the various embodiments of the methods, as described above. For example, a computer program product is described, the product comprising computer-readable instructions that, when executed in a computerized system comprising at least one processor, cause the processor to carry out one or more steps of any of the methods described above. In another example, a computerized system is described, the system comprising a processor configured with non-transitory computer-readable instructions that, when executed, cause the processor to carry out any of the methods described above. The computer program product and the computerized methods described herein may be implemented in a computerized system having one or more computing devices, each including one or more processors. Generally, the computerized systems described herein may comprise one or more engines, which include a processor or devices, such as a computer, microprocessor, logic device or other device or processor that is configured with hardware, firmware, and software to carry out one or more of the computerized methods described herein. Any one or more of these engines may be physically separable from any one or more other engines, or may include multiple physically separable components, such as separate processors on common or different circuit boards. The computer systems of the present invention comprises means for implementing the methods and its various embodiments as described above. The engines may be interconnected from time to time, and further connected from time to time to one or more databases, including a measurables database, an experimental data database and a literature database. The computerized system described herein may include a distributed computerized system having one or more processors and engines that communicate through a network interface. Such an implementation may be appropriate for distributed computing over multiple communication systems.

BRIEF DESCRIPTION OF THE DRAWINGS

Further features of the disclosure, its nature and various advantages, will be apparent upon consideration of the following detailed description, taken in conjunction with the accompanying drawings, in which like reference characters refer to like parts throughout, and in which.

DETAILED DESCRIPTION

To provide an overall understanding of the systems and methods described herein, certain illustrative embodiments will now be described, including systems and methods for identifying gene biomarker signatures. However, it will be understood by one of ordinary skill in the art that the systems and methods described herein may be adapted and modified for other suitable applications and that such other additions and modifications will not depart from the scope thereof.

The systems and methods described herein include techniques for generating both reproducible and interpretable gene signatures. The techniques involve resampling a data set and choosing genes having a high frequency of emergence. In particular, the systems and methods described herein include repeated sampling of data sets, ranking genes based on frequency of occurrence in gene signatures generated through the repeated sampling process, and iteratively selecting the best gene signature. Generally, the computerized systems described herein may comprise one or more engines, which include a processing device or devices, such as a computer, microprocessor, logic device or other device or processor that is configured with hardware, firmware, and software to carry out one or more of the computerized methods described herein.

Figure 1:
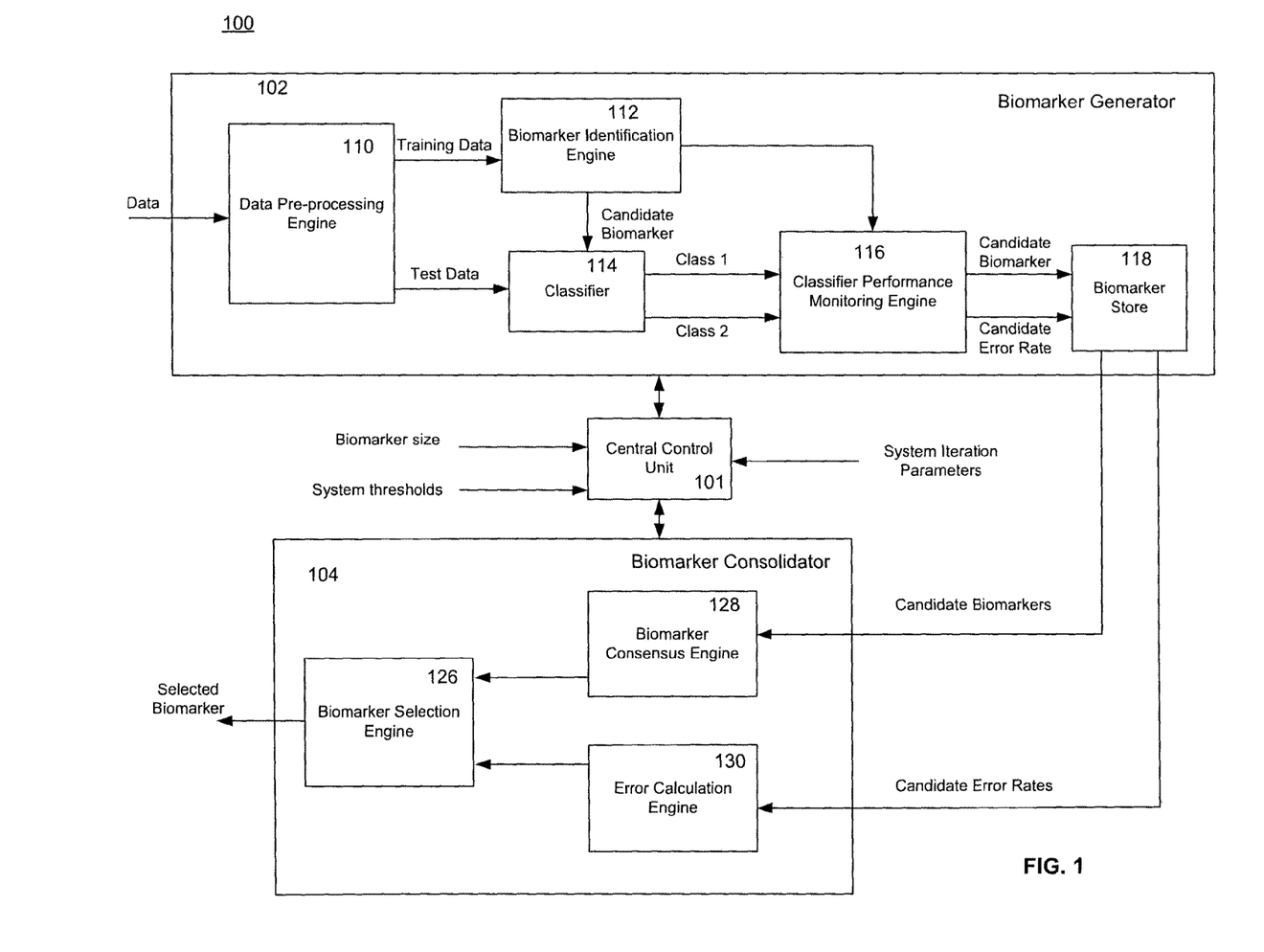
FIG. 1 depicts an exemplary system for identifying one or more biomarker signatures.

FIG. 1 depicts an exemplary system 100 for identifying one or more biomarker signatures. System 100 includes a biomarker generator 102 and a biomarker consolidator 104. The system 100 further includes a central control unit (CCU) 101 for controlling certain aspects of the operation of the biomarker generator 102 and the biomarker consolidator 104. During operation, data such as gene expression data is received at the biomarker generator 102. The biomarker generator 102 processes the data to generate a plurality of candidate biomarkers and corresponding error rates. The biomarker consolidator 104 receives these candidate biomarkers and error rates and selects a suitable biomarker having an optimal performance measure and size.

The biomarker generator 102 includes several components for processing data and generating a set of candidate biomarkers and candidate error rates. In particular, the biomarker generator includes a data pre-processing engine 110 for splitting the data into a training data set and a test data set. The biomarker generator 102 includes a biomarker identification engine 112 for receiving the training data set and generating candidate biomarkers, a classifier 114 for receiving the candidate biomarkers and classifying the test data into one of two classes (e.g., disease data and control data). The biomarker generator 102 includes a classifier performance monitoring engine 116 for determining the performance of the candidate biomarker against the test data selected by the data pre-processing engine 110. The classifier performance monitoring engine 116 generates performance measures, which may include candidate error rates, for one or more candidate biomarkers. The biomarker generator 102 further includes a biomarker store 118 for storing one or more candidate biomarkers and candidate performance measures.

The biomarker generator may be controlled by the CCU 101, which in turn may be automatically controlled or user-operated. In certain embodiments, the biomarker generator 102 may operate to generate a plurality of candidate biomarkers, each time splitting the data randomly into training and test data sets. To generate such a plurality of candidate biomarkers, the operation of the biomarker generator 102 may be iterated a plurality of times. CCU 101 may receive one or more system iteration parameters include a desired number of candidate biomarkers, which in turn may be used to determine the number of times the operation of the biomarker generator 102 may be iterated. The CCU 101 may also receive other system parameters including a desired biomarker size which may be representative of the number of components in a biomarker (e.g., the number of genes in a biomarker gene signature). The biomarker size information may be used by the biomarker identification engine 112 for generating candidate biomarkers from the training data. The operation of the biomarker generator 102 and its respective engines are described in more detail with reference to FIGS. 2-4.

The biomarker generator 102 generates one or more candidate biomarkers and candidate error rates, which is used by the biomarker consolidator 104 for generating robust biomarkers. The biomarker consolidator 104 includes a biomarker consensus engine 128 which receives a plurality of candidate biomarkers and generates a new biomarker signature having the most frequently occurring genes across the plurality of candidate biomarkers. The biomarker consolidator 104 includes an error calculation engine 130 for determining an overall error rate across the plurality of candidate biomarkers. Similar to the biomarker generator 102, the biomarker consolidator 104 may also be controlled by the CCU 101, which in turn may be automatically controlled or user-operated. The CCU 101 may receive, determine, or both, a suitable threshold values for the minimum biomarker size, and use this information to determine the number of iterations to operate both the biomarker generator 102 and the biomarker consolidator 104. In one embodiment, during each iteration, the CCU 101 decreases the biomarker size by one and iterates both the biomarker generator 102 and the biomarker consolidator 104 until the threshold is reached. In such an embodiment, the biomarker consensus engine 128 outputs a new biomarker signature and a new overall error rate for each iteration. The biomarker consensus engine 128 thus outputs set of new biomarker signatures each having a different size varying from the threshold value up to a maximum biomarker size. The biomarker consolidator 104 further includes a biomarker selection engine 126 which reviews the performance measure or error rate of each of these new biomarker signatures and selects the optimal biomarker for output. The operation of the biomarker consolidator 104 and its respective engines are described in more detail with reference to FIGS. 2-4.

Figure 2:
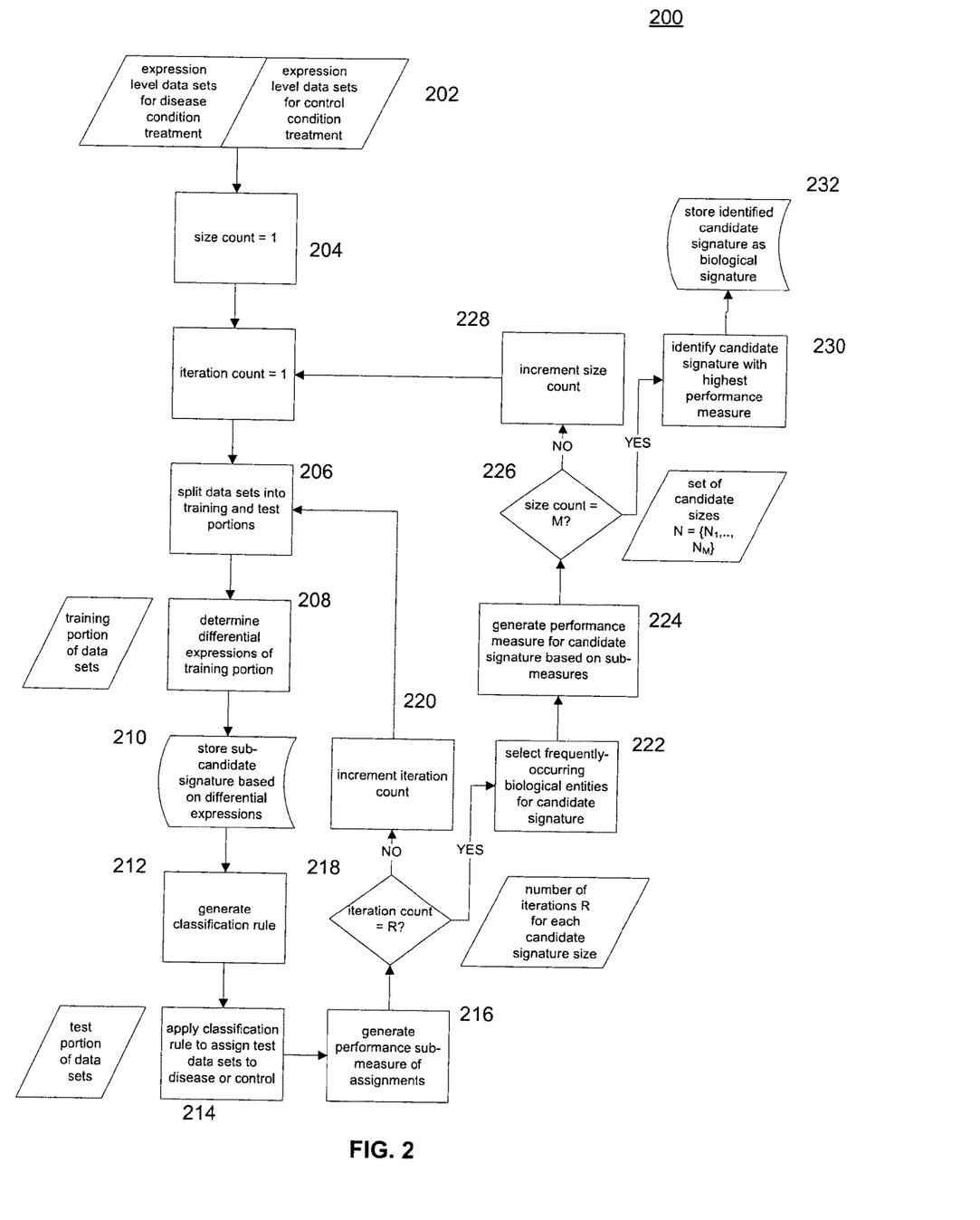
FIG. 2 depicts an exemplary process for identifying one or more biomarker signatures.

FIG. 2 depicts an exemplary process 200 for identifying one or more biomarker signatures using exemplary system 100 of FIG. 1. The process 200 begins with receiving one or more datasets at the data preprocessing engine 110 (step 202). Generally, the data may represent expression values of a plurality of different genes in a sample, a variety of a phenotypic characteristics such as levels of any biologically significant analyte, or both. In certain embodiments, the data sets may include expression level data for disease condition treatment and for control condition treatment. Gene expression level may refer to the amount of a molecule encoded by the gene, e.g., an RNA or polypeptide. The expression level of an mRNA molecule may include the amount of mRNA, which is determined by the transcriptional activity of the gene encoding the mRNA, and the stability of the mRNA, which in turn, is determined by the half-life of the mRNA. The gene expression level may also include the amount of a polypeptide corresponding to a given amino acid sequence encoded by a gene. Accordingly, the expression level of a gene can correspond to the amount of mRNA transcribed from the gene, the amount of polypeptide encoded by the gene, or both. Expression levels of a gene may be further categorized by expression levels of different forms of gene products. For example, RNA molecules encoded by a gene may include differentially expressed splice variants, transcripts having different start or stop sites, other differentially processed forms, or both. Polypeptides encoded by a gene may encompass cleaved, modified forms of polypeptides, or both. Polypeptides can be modified by phosphorylation, lipidation, prenylation, sulfation, hydroxylation, acetylation, ribosylation, farnesylation, addition of carbohydrates, and the like. Further, multiple forms of a polypeptide having a given type of modification can exist. For example, a polypeptide may be phosphorylated at multiple sites and express different levels of differentially phosphorylated proteins.

In certain embodiments the gene expression level in a cell or tissue may be represented by a gene expression profile. Gene expression profiles may refers to a characteristic representation of a gene's expression level in a specimen such as a cell or tissue. The determination of a gene expression profile in a specimen from an individual is representative of the gene expression state of the individual. A gene expression profile reflects the expression of messenger RNA or polypeptide or a form thereof encoded by one or more genes in a cell or tissue. An expression profile may generally refer to a profile of biomolecules (nucleic acids, proteins, carbohydrates) which shows different expression patterns among different cells or tissue.

In certain embodiments, the data sets may include elements representing gene expression values of a plurality of different genes in a sample. In other embodiments, the data set may include elements that represent peaks or heights of peaks detected by mass spectrometry. Generally, each data set may include a plurality of forms of at least one biological state class. For example, a biological state class can include, but is not limited to: presence/absense of a disease in the source of the sample (i.e., a patient from whom the sample is obtained); stage of a disease; risk for a disease; likelihood of recurrence of disease; a shared genotype at one or more genetic loci (e.g., a common HLA haplotype; a mutation in a gene; modification of a gene, such as methylation, etc.); exposure to an agent (e.g., such as a toxic substance or a potentially toxic substance, an environmental pollutant, a candidate drug, etc.) or condition (temperature, pH, etc); a demographic characteristic (age, gender, weight; family history; history of preexisting conditions, etc.); resistance to agent, sensitivity to an agent (e.g., responsiveness to a drug) and the like.

Data sets may be independent of each other to reduce collection bias in ultimate classifier selection. For example, they can be collected from multiple sources and may be collected at different times and from different locations using different exclusion or inclusion criteria, i.e., the data sets may be relatively heterogeneous when considering characteristics outside of the characteristic defining the biological state class. Factors contributing to heterogeneity include, but are not limited to, biological variability due to sex, age, ethnicity; individual variability due to eating, exercise, sleeping behavior; and sample handling variability due to clinical protocols for blood processing. However, a biological state class may comprise one or more common characteristics (e.g., the sample sources may represent individuals having a disease and the same gender or one or more other common demographic characteristics).

In certain embodiments, the data sets from multiple sources are generated by collection of samples from the same population of patients at different times, under different conditions, or both. However, data sets from multiple sources do not comprise a subset of a larger data set, i.e., data sets from multiple sources are collected independently (e.g., from different sites, at different times, under different collection conditions, or a combination of the foregoing).

In certain embodiments, a plurality of data sets is obtained from a plurality of different clinical trial sites and each data set comprises a plurality of patient samples obtained at each individual trial site. Sample types include, but are not limited to, blood, serum, plasma, nipple aspirate, urine, tears, saliva, spinal fluid, lymph, cell, tissue lysates, laser microdissected tissue or cell samples, embedded cells or tissues (e.g., in paraffin blocks or frozen); fresh or archival samples (e.g., from autopsies), or a combination of the foregoing. A sample can be derived, for example, from cell or tissue cultures in vitro. Alternatively, a sample can be derived from a living organism or from a population of organisms, such as single-celled organisms.

In one example, when identifying biomarkers for a particular cancer, blood samples for might be collected from subjects selected by independent groups at two different test sites, thereby providing the samples from which the independent data sets will be developed.

Returning to FIG. 2, in certain embodiments, it may be desirable to use the biomarker to classify between the disease condition treatment and a control condition treatment. In such embodiments, the data may include, for example, expression level data sets for disease condition treatment and for control condition treatment. CCU 101 may set system parameters including the size of count of each iteration, the number of iterations and the initial iteration count (step 204). In one example, the size and iteration count are set to 1.

The data pre-processing engine 110 receives the data and splits the data into a training data set and a test data set (step 206). In certain embodiments, the data pre-processing engine 110 randomly splits or divides the data into these two groups. Randomly dividing the data may be desirable for predicting classes and generating robust gene signature. In other embodiments, the data pre-processing engine 110 separates the data into two or more groups based on the type or label of the data. Generally, the data can be separated into a training data set and a test data set in any suitable way as desired without departing from the scope of the present disclosure. The training data set and the test data set may have any suitable size and may be of the same or different sizes. In certain embodiments, the data pre-processing engine 110 may discard one or more pieces of data prior to splitting the data into the training and test data sets. In certain embodiments, the data pre-processing engine 110 may discard one or more pieces of data from the training data set, the test data set or both prior to any further processing.

The data pre-processing engine 110 passes along the training data sets to the biomarker identification engine 112, which identifies candidate networks (step 208). The biomarker identification engine 112 also receives a biomarker size. In certain embodiments, the biomarker size may be selected to be the maximum allowable biomarker size, with system 100 iterating and counting down to a minimum biomarker size. In certain embodiments, the biomarker identification engine 112, uses a suitable statistical technique to determine the differential expressions of the training data. For example, each training data may include a plurality of training data sets, with each training data set including a probe set for a plurality of genes. For each of the plurality of genes, the data sets include a known value corresponding to a control and another value for a treatment. In certain embodiments, the biomarker identification engine 112 determines, across the plurality of training data sets, for each gene, the distance between control value and treatment value. The distance may be measured by t statistics, such as a moderate t statistics calculated by SAM or Limma. Limma is a software method package well known for the analysis of gene expression microarray data, especially the use of linear models for analyzing differential expression (Smyth 2004, Statistical Applications in Genetics and Molecular Biology, Vol. 3, No. 1, Article 3, which is incorporated herein by reference in its entirety). Limma is preferred due to its efficiency and lower demand on computing power than SAM. The biomarker identification engine 112 may then rank the genes by their t statistics. In certain embodiments, a high ranking may represent that the gene is highly differentially expressed between control and treatment, and a low ranking may represent that there is little difference between the control and treatment for that gene. The biomarker identification engine 112 may select a portion of the ranked list of genes, for example, the top half of the gene list. The number of genes selected by the biomarker identification engine 112 may be based on the biomarker size input by the CCU 101. In one example, one or more transcription factors, i.e., master-regulator genes may be selected. The selected genes may then be representative or may constitute the candidate biomarker. The biomarker identification engine 112 may output the candidate biomarker to the classifier 114, classifier performance monitoring engine 116 and the biomarker store 118 (step 210).

Figure 3:
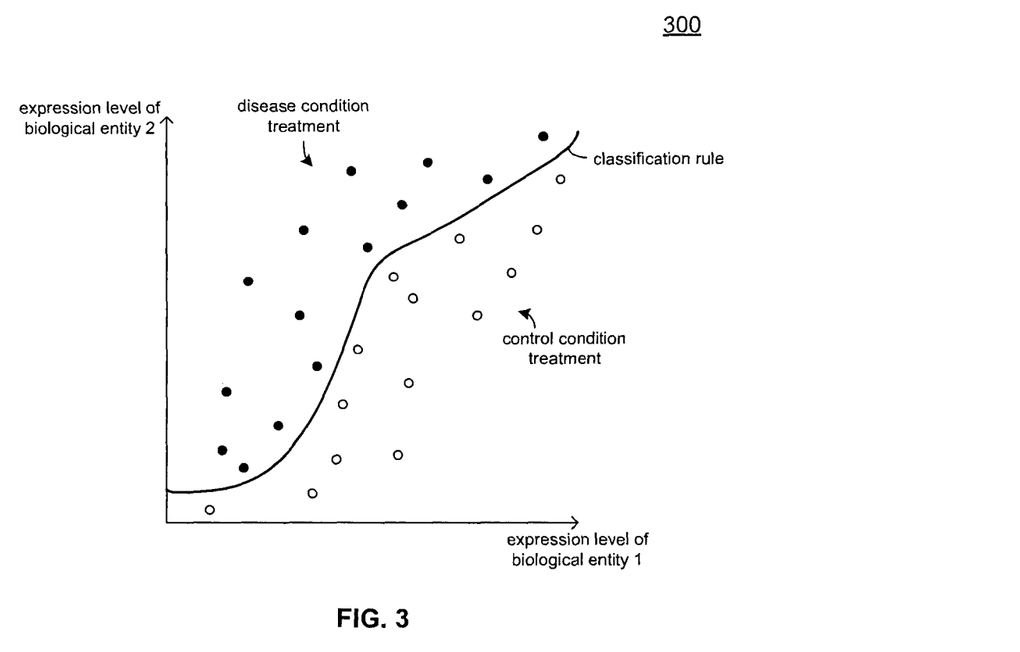
FIG. 3 is a graph depicting the classification of data samples and the determination of a classification rule.

The classifier 114 may receive one or more candidate biomarkers from the biomarker identification engine 112. The classifier 114 may also receive one or more sets of test data from the data pre-processing engine 110. In certain embodiments, the classifier 114 uses the candidate biomarker to generate a classification rule (step 212). FIG. 3 depicts, graphically such a classification rule 300. The classifier 114 may apply the classification rule to assign test data sets to either one of two classes. For example, the classifier 114 may apply the classification to assign test data sets to either disease or control (step 214). In certain embodiments, the classifier 114 may include a support vector machine (SVM) classifier. In other embodiments, the classifier 114 may include network-based SVMs, neural network-based classifiers, logistic regression classifier, decision tree-based classifier, classifiers employing a linear discriminant analysis technique, a random-forest analysis technique, or a combination of the foregoing.

The classifier performance monitoring engine 116 may analyze the performance of the classifier 114 using a suitable performance metric (step 216). In particular, when analyzing the performance of the classifier 114, the classifier performance monitoring engine 116 may be analyzing the robustness or performance of one or more candidate biomarkers. In certain embodiments, the performance metric may include an error rate. The performance metric may also include the number of correct predictions divided by the total predictions attempted. The performance metric may be any suitable measure without departing from the scope of the present disclosure. The candidate biomarker and the corresponding performance metric may be stored in biomarker store 118.

In certain embodiments, the process from steps 206-step 216 may be repeated any number of times to generate a plurality of candidate biomarkers along with corresponding performance metrics. During each repetition, the data may be randomly divided into a training set and a test data set. The CCU 101 may control the operation of the biomarker generator 102 to perform such repeated analysis. In certain embodiments, the CCU 101 may provide a fixed iteration count (step 218), R. In such embodiments, R candidate biomarkers may be generated through repetition, each time increasing the iteration number (step 220). Once the iterations have been completed, CCU 101, the biomarker generator 102, or both, may calculate a composite performance score of all the candidate biomarkers. The composite performance score may be an average of the performance metrics of the candidate biomarkers. In certain embodiments, the data sets may be unbalanced (i.e., unequal number of different states, for example, treatments and controls). In such embodiments, the performance score may be determined using a Matthew correlation coefficient (MCC).

$$MCC = \frac{TP*TN - FP*FN}{\sqrt{(TP+FP)*(TP+FN)*(TN+FP)*(TN+FN)}}$$

Where TP: true positive; FP: false positive; TN: true negative; FN: false negative.

As noted earlier, the CCU 101 may also control the operation of the biomarker consolidator 104 for generating a suitable and robust biomarker based on the candidate biomarkers generated and stored in the biomarker generator 102. The biomarker consolidator 104 includes a biomarker consensus engine 128, which receives one or more candidate biomarkers from the biomarker store 118. The biomarker consensus engine 128 may select frequently occurring genes within the one or more candidate biomarkers for a new biomarker signature (step 222). The new biomarker signature may include an N number of genes, where N is a desired size of the biomarker, the maximum allowed size of the biomarker, a minimum allowed size of the biomarker or a size between the maximum and minimum sizes. In certain embodiments, the number N may be user-selectable and may be adjustable as desired.

In certain embodiments, the biomarker consensus engine 128 calculates the frequency of each gene based on its appearance across all the candidate biomarkers. Mathematically, the biomarker consensus engine 128 may take the union of genes in the candidate networks and then calculate the frequency of occurrence of each of the genes as follows:

$$r_{j,N} = \frac{\sum_{iter=1}^{R} f(j, iter, N) \times P(N, iter)}{R},$$

$$f(j, iter, N) = 1, j \in GS(N, iter); 0, j \notin GS(N, iter)$$

Where $r_{j,N}$ is the overall weighted frequency of gene j when we choose N top genes; GS(N, iter) is the sub gene signature with N top genes for iteration iter; P(N, iter) is the prediction performance of GS(N, iter) in test data. The biomarker consensus engine 128 may generate a list of genes ranked by their frequency of occurrence across the candidate biomarkers.

The biomarker consensus engine 128 may select a subset of this list to form a new biomarker signature of a desired length. The error calculation engine 130 determines an overall performance metric of all the candidate biomarkers (step 224). The overall performance metric may be the same as the composite score determined by the biomarker generator 102, as described above.

Figure 4:
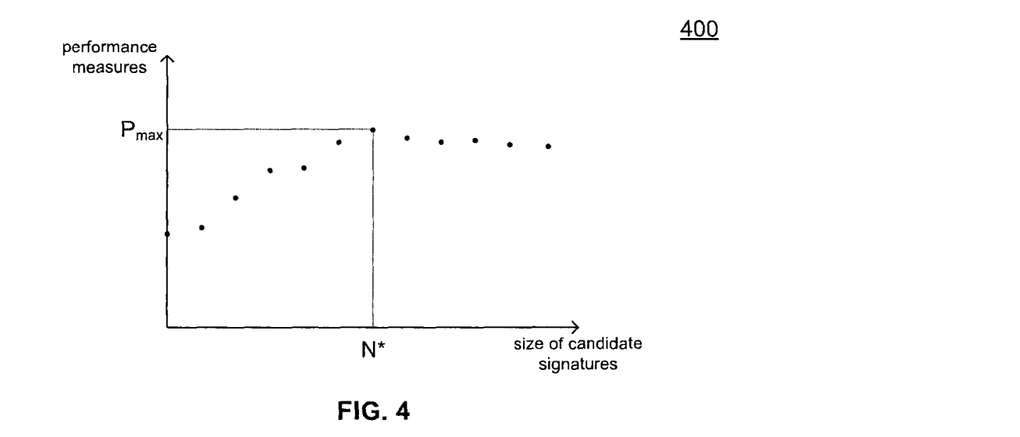
FIG. 4 is a graph depicting the performance of a plurality of biomarker signatures, each having a different number of components.

One challenge faced by researchers when identifying biomarkers is determining its size. Each disease scenario may warrant a different sized biomarker and therefore it may be difficult for researchers to confidently decide how long a biomarker should be. Inventors have recognized that a solution to this problem is to iterate through various sizes of biomarkers and arrive at one that best predicts and classifies test data. In certain embodiments, a user may select a maximum biomarker signature size and a minimum biomarker signature size. The system 100 may iterate through each of the sizes between the maximum and minimum biomarker signature sizes. During each iteration, the biomarker consensus engine 128 may generate a new biomarker signature and the error calculation engine 130 may generate a corresponding performance score for the new biomarker signature. In certain embodiments, system 100 may start from the maximum size and count down to the minimum size. In other embodiments, the system 100 may start from the minimum size and iterate up to the maximum size. The system 100 may choose to skip certain sizes or may repeat certain sizes, without departing from the scope of the present disclosure. The biomarker selection engine 126 may then select a suitable new biomarker signature from the set of biomarker signatures having the highest performance measure (step 230). FIG. 4 graphically depicts the operation of the biomarker selection engine 126. In particular, FIG. 4 shows a graph of the new biomarker signatures generated by the biomarker consensus engine 128 and the corresponding performance measure generated by the error calculation engine 130. Biomarker signature of N* length was selected because it has the highest performance measure value.

Figure 5:
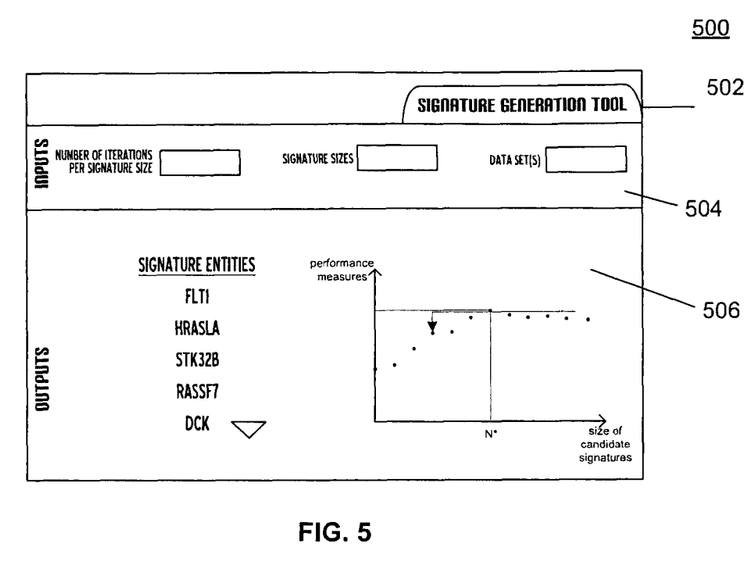
FIG. 5 is a screenshot of an exemplary biomarker signature generation tool.

FIG. 5 is a screenshot 500 of a tool used to identify and generate biomarker signatures. The tool may be implemented on a computer whereby the back-end is system 100 and the front end displays the graphical user interface (GUI) depicted in screenshot 500. The GUI may be used to allow a user to interact with system 100 and thereby provide data sets and receive information about potential biomarker signatures. For example, the GUI may include a label 502 identifying the screen or program, an input region 504 and an output region 506. The input region 504 includes one or more text boxes, labels, drop-down menus, radio-buttons, command buttons, or a combination of the foregoing, for allowing a user to input one or more variables, parameters or metrics of system 100. For example, the input region 504 may include components a user to enter the number of times that biomarker generator 102, biomarker consolidator 104, or both, should iterate through prior to completing the process. The input region 504 may also allow a user to enter the maximum, minimum or any suitable signature size. The input region 504 also allow the user to provide one or more data sets by uploading from local disk or remote disk. The GUI may also include an output region 506 which may include a display of one or more candidate biomarkers, new biomarker signatures, final biomarker signatures, or both. The output region 506 may also include one or more graphs including graphs depicted in FIGS. 3 and 4. Generally, the GUI may include any input, output, or both, from any component in the system 100. The GUI may also allow for any other computing operations including power management, communication, display, storage and data management.

EXAMPLE

In one example, the systems and methods described herein, including system 100, were used to generate and identify a gene signature that helps distinguish ex-smokers from current smokers of tobacco products. In such an example, data supplied to the Data Pre-processing Engine 110 included publicly-available data from University of Texas, M. D. Anderson Cancer Center. Such data is described in the "Impact of smoking cessation on global gene expression in the bronchial epithelium of chronic smokers," Zhang L, et al., Cancer Prev. Res. 1:112-118, 2008, which is incorporated herein by reference in its entirety. The data was generated by sampling the airway of 13 healthy smokers (HS) and 8 healthy ex-smokers (HExS), i.e., those who quit smoking more than 12 months before sampling was performed. The sampled set of smokers and ex-smokers were 78% white and 61% male. To obtain the data, RNA isolation from airways was hybridized to Affymetrix GeneChip® Human Genome U133 Plus 2.0 Array.

System 100 was set-up to analyze this data and generate a gene signature that would help distinguish smokers form ex-smokers. In this example, the biomarker size, which includes the maximal size of a signature, was set at 500, and input into the CCU 101. The system iteration parameters including maximal number of resamplings was set to 300. The Data Pre-processing Ending 110 randomly split the data into a test data set including about 10% of the data and a training data set including the remaining about 90% of the data. In the example, the classifier 114 was selected to be an SVM classifier such as the classifier described in "Support-vector networks. Machine learning," Cortes, C. and V. Vapnik, 1995. 20(3): p. 273-297, which is incorporated herein by reference in its entirety. For ranking genes, the system 100 included a suitable SAM engine, such as an SAM described in "Significance analysis of microarrays applied to the ionizing radiation response," Tusher, V. G., R. Tibshirani, and G. Chu, Proc Natl Acad Sci USA, 2001. 98(9): p. 5116-21, which is incorporated herein by reference in its entirety.

Figure 6:
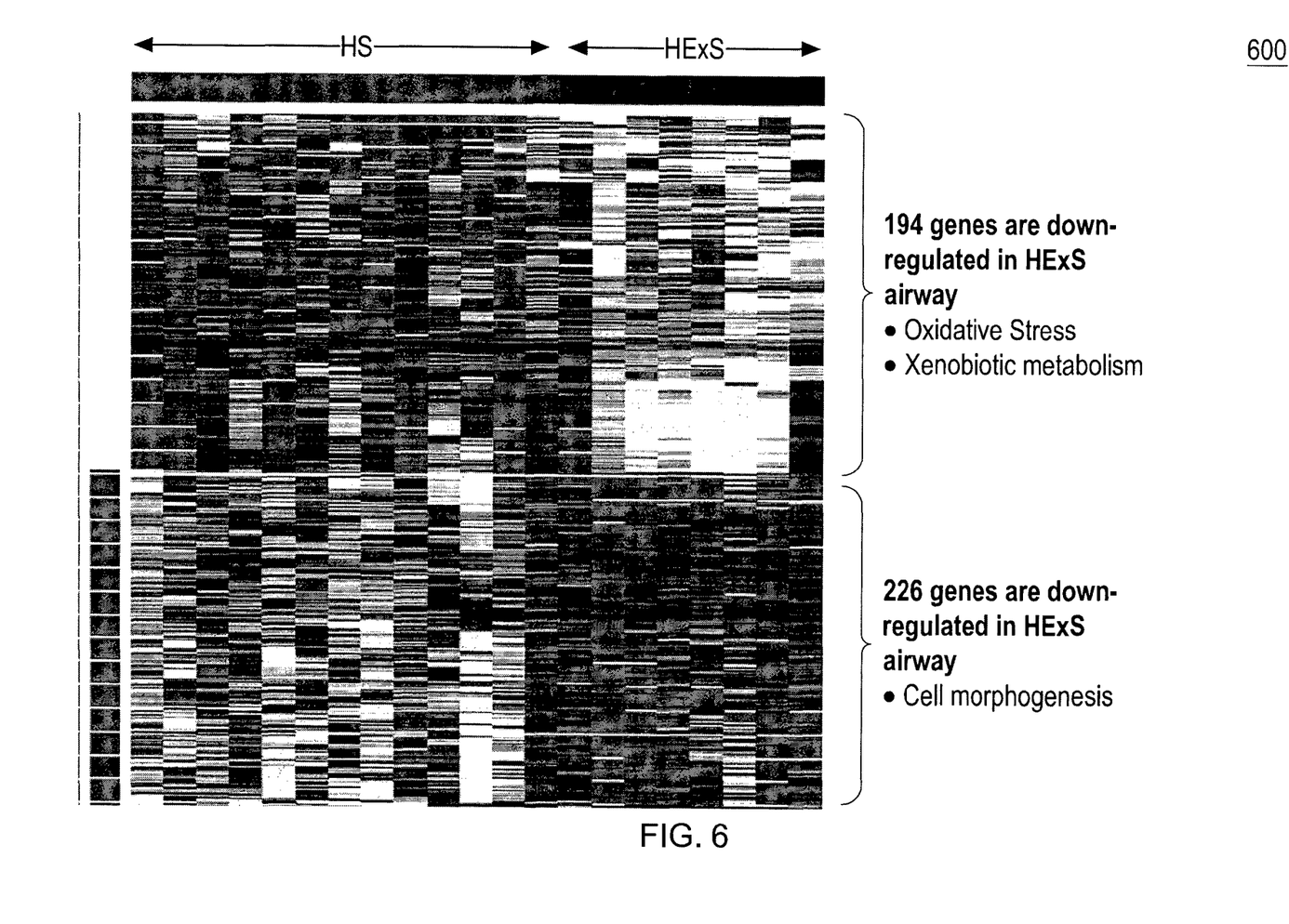
FIG. 6 shows a heatmap of an exemplary 420-gene signature biomarker generated by the system of FIG. 1.

The system 100 according to the methods of the invention generated a stable 420-gene signature that distinguishes ex-smokers from current smokers. The generated signature was the highest performing signature in the set of candidate signatures having a size less than or equal to 500. FIG. 6 shows a heatmap of the 420-gene signature 600. The colors of the heatmap may not be clearly shown in grey scale, but the data of FIG. 6 show that 194 genes, in which oxidative stress and xenobiotic metabolism are enriched, are down-regulated in healthy ex-smokers (HExS) airway; 226 genes, in which cell morphogenesis is enriched, are up-regulated in HExS airway. The heatmap shown in FIG. 6 may be displayed in user interface 500.

Implementations of the present subject matter can include, but are not limited to, systems methods and computer program products comprising one or more features as described herein as well as articles that comprise a machine-readable medium operable to cause one or more machines (e.g., computers, robots) to result in operations described herein. The methods described herein can be implemented by one or more processors or engines residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems.

Figure 7:
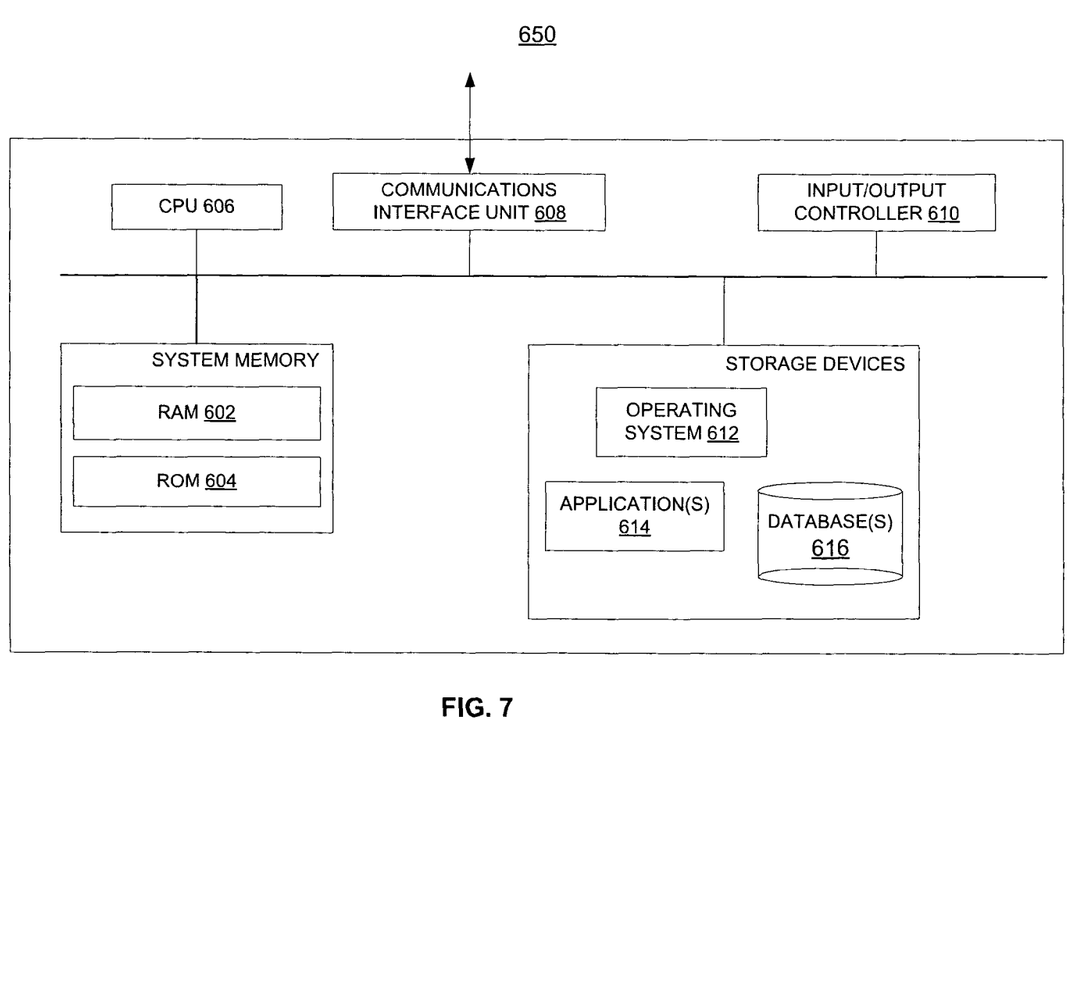
FIG. 7 is a block diagram of a computing device, such as any of the components of the system of FIG. 1 and screenshot of FIG. 5.

FIG. 7 is a block diagram of a computing device, such as any of the components of system 100 of FIG. 1 and GUI 500 of FIG. 5 including circuitry for performing processes described with reference to FIGS. 2-4. Each of the components of system 100 may be implemented on one or more computing devices 650. In certain aspects, a plurality of the above-components and databases may be included within one computing device 650. In certain implementations, a component and a database may be implemented across several computing devices 650.

The computing device 650 comprises at least one communications interface unit, an input/output controller 610, system memory, and one or more data storage devices. The system memory includes at least one random access memory (RAM 602) and at least one read-only memory (ROM 604). All of these elements are in communication with a central processing unit (CPU 606) to facilitate the operation of the computing device 650. The computing device 650 may be configured in many different ways. For example, the computing device 650 may be a conventional standalone computer or alternatively, the functions of computing device 650 may be distributed across multiple computer systems and architectures. The computing device 650 may be configured to perform some or all of data-splitting, differentiating, classifying, scoring, ranking and storing operations. In FIG. 7, the computing device 650 is linked, via network or local network, to other servers or systems.

The computing device 650 may be configured in a distributed architecture, wherein databases and processors are housed in separate units or locations. Some such units perform primary processing functions and contain at a minimum a general controller or a processor and a system memory. In such an aspect, each of these units is attached via the communications interface unit 608 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 606 comprises a processor, such as one or more conventional microprocessors and one or more supplementary co-processors such as math co-processors for offloading workload from the CPU 606. The CPU 606 is in communication with the communications interface unit 1008 and the input/output controller 610, through which the CPU 606 communicates with other devices such as other servers, user terminals, or devices. The communications interface unit 608 and the input/output controller 610 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 606 is also in communication with the data storage device. The data storage device may comprise an appropriate combination of magnetic, optical or semiconductor memory, and may include, for example, RAM 602, ROM 604, flash drive, an optical disc such as a compact disc or a hard disk or drive. The CPU 606 and the data storage device each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 606 may be connected to the data storage device via the communications interface unit 608. The CPU 606 may be configured to perform one or more particular processing functions.

The data storage device may store, for example, (i) an operating system 1012 for the computing device 650; (ii) one or more applications 614 (e.g., computer program code or a computer program product) adapted to direct the CPU 606 in accordance with the systems and methods described here, and particularly in accordance with the processes described in detail with regard to the CPU 606; or (iii) database(s) 616 adapted to store information that may be utilized to store information required by the program. In some aspects, the database(s) includes a database storing experimental data, and published literature models.

The operating system 612 and applications 614 may be stored, for example, in a compressed, an uncompiled and an encrypted format, and may include computer program code. The instructions of the program may be read into a main memory of the processor from a computer-readable medium other than the data storage device, such as from the ROM 604 or from the RAM 602. While execution of sequences of instructions in the program causes the CPU 606 to perform the process steps described herein, hard-wired circuitry may be used in place of, or in combination with, software instructions for implementation of the processes of the present invention. Thus, the systems and methods described are not limited to any specific combination of hardware and software.

Suitable computer program code may be provided for performing one or more functions in relation to modeling, scoring and aggregating as described herein. The program also may include program elements such as an operating system 612, a database management system and "device drivers" that allow the processor to interface with computer peripheral devices (e.g., a video display, a keyboard, a computer mouse, etc.) via the input/output controller 610.

A computer program product comprising computer-readable instructions is also provided. The computer-readable instructions, when loaded and executed on a computer system, cause the computer system to operate according to the methods, or one or more steps of the methods described above. The term "computer-readable medium" as used herein refers to any non-transitory medium that provides or participates in providing instructions to the processor of the computing device 650 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 606 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 650 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

While implementations of the invention have been particularly shown and described with reference to specific examples, it should be understood by those skilled in the art that various changes in form and detail may be made therein without departing from the spirit and scope of the disclosure.

The invention claimed is:

1. A computer-implemented method of identifying a biological signature for a disease state, comprising:
   (a) receiving, by a central control unit, a plurality of data sets, each data set comprising an expression level for a plurality of biological entities in a biological system in different states comprising a disease state and a control state;
   (b) for each of a plurality of iterations:
      (i) splitting, by a data processing engine in communication with the central control unit, the plurality of data sets into a training portion and a test portion, wherein the training portion of the plurality of data sets stores a predetermined number of biological entities with differential expressions above a threshold as a sub-candidate signature,
      (ii) generating, by a classifier device in communication with the data processing engine, a classification rule that assigns each of the data sets to one of a disease class and a control class based on the training portion of the plurality of data sets,
      (iii) assigning, by the classifier device, each data set to one of the disease class and the control class using the test portion of the plurality of data sets and the classification rule, and
      (iv) generating, by a classifier performance engine in communication with the classifier device, a performance sub-measure associated with the sub-candidate signature for the classification rule based on the assignment;
   (c) generating, by a biomarker generator, a candidate signature having the predetermined number of biological entities by calculating, for each biological entity in a set union of all of the biological entities included in the sub-candidate signatures having the predetermined number of biological entities, a weighted frequency and selecting frequently-identified biological entities based on the weighted frequency, the weighted frequency based on:
      (i) an appearance of the biological entity in the selected sub-candidate signature having the predetermined number of biological entities, and
      (ii) the generated performance sub-measure,
   wherein the biomarker generator comprises the central control unit, the data processing engine, the classifier device, and the classifier performance engine; (d) generating, by the biomarker generator, a performance measure associated with the candidate signature based on the performance sub-measures;
   (e) repeating steps (b) through (d) for a plurality of different values of the predetermined number of biological entities to generate, by the biomarker generator, a plurality of candidate signatures and a plurality of associated performance measures; and
   (f) storing, by the biomarker generator, as the biological signature, the candidate signature associated with a highest performance measure.

2. The method of claim 1, further comprising using the training portion to determine a differential expression for each biological entity by comparing the corresponding disease state expression level and the corresponding control state expression level.

3. The method of claim 1, wherein the classification rule assigns each of the data sets based on the expression levels of the biological entities within the data set.

4. The method of claim 1, wherein the performance sub-measure is generated by comparing the assignment for each data set against the different states associated with the data set.

5. The method of claim 1, wherein the plurality of biological entities comprises one or more of genes, miRNAs, proteins or a combination of two or more of the foregoing.

6. The method of claim 1, wherein an expression level comprises one or more of methylation data, gene expression data, miRNA expression data and protein expression data.

7. The method of claim 1, wherein determining a differential expression comprises at least one of a Significance Analysis of Microarrays (SAM) analysis and a Limma analysis.

8. The method of claim 1, wherein generating a classification rule comprises a support vector machine method.

9. The method of claim 1, wherein generating the performance sub-measure comprises calculating the percentage of data sets correctly assigned.

10. The method of claim 1, wherein generating the performance sub-measure comprises calculating a Matthews correlation coefficient of the assigned data sets.

11. The method of claim 1, wherein generating the performance measure comprises averaging all of the performance sub-measures for the sub-candidate signatures associated with the predetermined number.

12. The method of claim 1, further comprising displaying, on a display device, a graph of the plurality of performance measures against the plurality of different values of the predetermined number, and optionally a list of the biological entities included in the candidate signature.

13. A computer program product comprising computer-readable instructions that, when executed in a computerized system comprising a biomarker generator comprising a central control unit, a data processing engine, a classifier device, and a classifier performance engine, cause the processor to carry out a method comprising:
   (a) receiving, by the central control unit; a plurality of data sets, each data set comprising an expression level for a plurality of biological entities in a biological system in different states comprising a disease state and a control state;

(b) for each of a plurality of iterations:
(i) splitting, by the data processing engine in communication with the central control unit, the plurality of data sets into a training portion and a test portion, wherein the training portion of the plurality of data sets stores a predetermined number of biological entities with differential expressions above a threshold as a sub-candidate signature,
(ii) generating, by the classifier device in communication with the data processing engine, a classification rule that assigns each of the data sets to one of a disease class and a control class based on the training portion of the plurality of data sets,
(iii) assigning, by the classifier device, each data set to one of the disease class and the control class using the test portion of the plurality of data sets and the classification rule, and
(iv) generating, by the classifier performance engine in communication with the classifier device, a performance sub-measure associated with the sub-candidate for the classification rule based on the assignment;

(c) generating, by the biomarker generator, a candidate signature having the predetermined number of biological entities by calculating, for each biological entity in a set union of all of the biological entities included in the sub-candidate signatures having the predetermined number of biological entities, a weighted frequency and selecting frequently-identified biological entities based on the weighted frequency; the weighted frequency based on:
(i) an appearance of the biological entity in the selected sub-candidate signature having the predetermined number of biological entities, and
(ii) the generated performance sub-measure, (d) generating, by the biomarker generator, a performance measure associated with the candidate signature based on the performance sub-measures;

(e) repeating steps (b) through (d) for a plurality of different values of the predetermined number of biological entities to generate, by the biomarker generator, a plurality of candidate signatures and a plurality of associated performance measures; and (f) storing, by the biomarker generator, as the biological signature, the candidate signature associated with a highest performance measure.

14. A computerized system comprising a biomarker generator comprising:

a central control unit configured to receive a plurality of data sets, each data set comprising an expression level for a plurality of biological entities in a biological system in different states comprising a disease state and a control state;

a data processing engine in communication with the central control unit and configured to split the plurality of data sets into a training portion and a test portion, wherein the training portion of the plurality of data sets stores a predetermined number of biological entities with differential expressions above a threshold as a sub-candidate signature, a classifier device in communication with the data processing engine and configured to generate a classification rule that assigns each of the data sets to one of a disease class and a control class based on the training portion of the plurality of data sets; and a classifier performance engine in communication with the classifier device and configured to generate a performance sub-measure associated with the sub-candidate for the classification rule based on the assignment, wherein the biomarker generator is configured to generate a candidate signature having the predetermined number of biological entities by calculating, for each biological entity in a set union of all of the biological entities included in the sub-candidate signatures having the predetermined number of biological entities, a weighted frequency and selecting frequently-identified biological entities based on the weighted frequency; the weighted frequency based on:

(i) an appearance of the biological entity in the selected sub-candidate signature having the predetermined number of biological entities, and
(ii) the generated performance sub-measure, wherein the biomarker generator is configured to generate a performance measure associated with the candidate signature based on the performance sub-measures, wherein the biomarker generator is configured to generate a plurality of candidate signatures and a plurality of associated performance measures using a plurality of different values of the predetermined number of biological entities, and wherein the biomarker generator stores as the biological signature, the candidate signature associated with a highest performance measure.

* * * * *